United States Patent [19]

Busby

[11] 4,434,341
[45] Feb. 28, 1984

[54] SELECTIVE, LOCALLY DEFINED HEATING OF A BODY

[76] Inventor: Dennis L. Busby, Papenbuderstr. 25, 2000 Hamburg 76, Fed. Rep. of Germany

[21] Appl. No.: 215,445

[22] Filed: Dec. 11, 1980

[30] Foreign Application Priority Data

Feb. 20, 1980 [DE] Fed. Rep. of Germany ....... 3006356
Aug. 11, 1980 [DE] Fed. Rep. of Germany ....... 3030327

[51] Int. Cl.³ .......................... H05B 6/72; A61N 5/02
[52] U.S. Cl. ...................... 219/10.55 A; 219/10.55 R; 219/10.55 F; 219/121 LS; 219/121 LV; 128/1.3; 128/804; 250/498.1; 250/494.1; 248/183; 248/184
[58] Field of Search ................ 219/10.55 A, 10.55 R, 219/10.55 B, 10.55 M, 10.55 F, 121 L, 121 LS, 121 M, 121 LR, 121 LU, 121 LV, 121 LX, 121 LP; 128/804, 783, 662, 663, 1.3, 1.5; 250/453.1, 454.1, 455.1, 491.1, 494.1, 495.1, 498.1; 248/183, 182, 184–186

[56] References Cited

U.S. PATENT DOCUMENTS

| | | | |
|---|---|---|---|
| 2,860,251 | 11/1958 | Pakswer et al. | 219/121 LP |
| 3,148,265 | 9/1964 | Hansen | 219/121 LP |
| 3,316,119 | 4/1967 | Anderson et al. | 219/10.55 F |
| 3,378,446 | 4/1968 | Whittlesey | 219/121 LS |
| 3,397,296 | 8/1968 | Corran | 219/10.55 F |
| 3,466,439 | 9/1969 | Setala | 250/454.1 |
| 3,552,382 | 1/1971 | Mount | 128/662 |
| 3,648,009 | 3/1972 | Steigerwald | 219/121 |
| 3,821,555 | 6/1974 | Mattsson | 250/494.1 |
| 3,861,763 | 1/1975 | Perkins | 248/183 |
| 4,215,694 | 8/1980 | Isakov et al. | 219/121 LX |
| 4,230,129 | 10/1980 | LeVeen | 128/804 |
| 4,314,128 | 2/1982 | Chitre | 219/10.55 B |
| 4,316,474 | 2/1982 | Spethmann | 128/804 |
| 4,337,661 | 7/1982 | Kretz | 128/663 |
| 4,343,995 | 8/1982 | Klausz | 250/491.1 |

FOREIGN PATENT DOCUMENTS

52-19342 2/1977 Japan ........................... 219/10.55 R

Primary Examiner—B. A. Reynolds
Assistant Examiner—Philip H. Leung
Attorney, Agent, or Firm—Cushman, Darby & Cushman

[57] ABSTRACT

An apparatus and method are provided for the selective, locally defined heating of an object, particularly a human body to destroy malignant cells of the body. A ring has a plurality of high frequency antennas or the like mounted on the inner surface thereof, capable of focusing together at a common volume. The transmitters may be mounted for limited pivotal movement, and for radial movement, with respect to the ring to provide flexibility in focusing. The ring is preferably disposed generally vertically, and is mounted so that it is rotatable about its center, and pivotal about two perpendicular axes disposed in the plane of the ring, and is mounted for reciprocal movement in a dimension perpendicular to the plane of the ring. A human body is disposed within the ring and energy is supplied to the transmitters to focus on the malignant cells of the human body, and destroy them. Various structures for enhancing the focusing effect may be provided.

15 Claims, 9 Drawing Figures

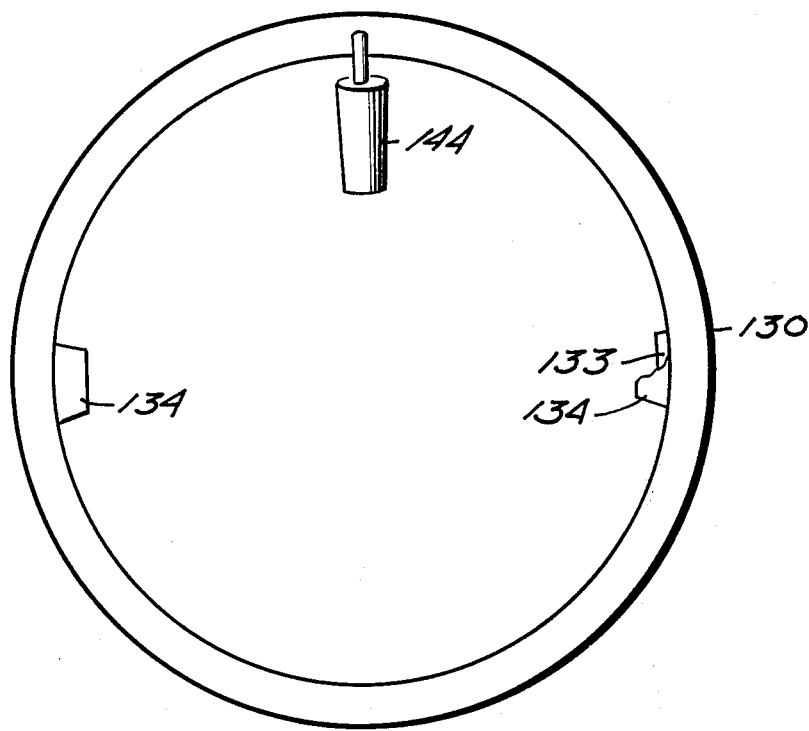
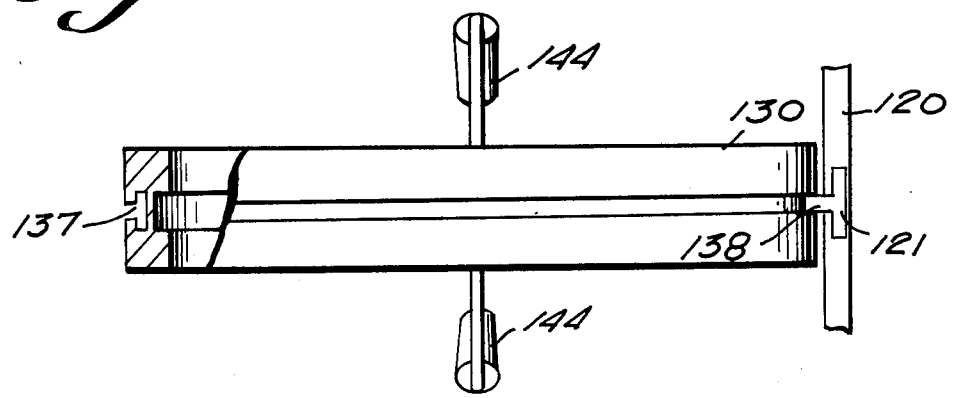

SELECTIVE, LOCALLY DEFINED HEATING OF A BODY

BACKGROUND AND SUMMARY OF THE INVENTION

The invention relates to an apparatus and method for the selective, locally defined heating of an object. The invention is particularly applicable to the destruction of malignant cells or tumors in a human body by the local heating of the cells or tumors. Heretofore, it has not been possible to effect destruction of malignant tumors or the like by local heating thereof without having to operate, cutting open the body.

The apparatus according to the present invention is capable of destroying malignant cells or tumors located within a body by selective, locally defined heating, while the tissues surrounding the malignant cells or tumors are not destroyed. The apparatus and method according to the present invention can be used in conjunction with other treatments, such as medications which prevents cell division, or ionizing radiation.

High frequency radiation, is eminently suited for the practice of the present invention since, it acts in the preferred manner within the depth of the body, and does not cause burns on the surface of the skin, and complex heating fields can be built-up within the body by using a plurality of transmitters focused at the same general volume. Additionally, according to the present invention, the desirable irradiation is accomplished with a minimum expenditure of energy, and low transmitting power. The transmitters simultaneously irradiate energy on a defined volume so that there is an energy concentration at the defined volume which is well beyond the transmitting power of each of the individual transmitters, resulting in destruction of the malignant cells or tumors (which have a lower tolerance to such radiation than healthy cells) while not harming the surrounding normal tissue.

To accomplish the desired effects, according to the present invention a plurality of high frequency heat radiation-emitting transmitters are mounted to an inner surface of a ring in such a way that radiation beams emitted by the transmitters intersect each other generally within a common volume, which common volume is generally encompassed by the ring. Preferably the transmitters are microwave antennas, solid-state antennas being preferred since they have a low continuous power output but a high pulse power output. Such antennas which are capable of emitting a few milliwatts of microwave energy in continuous operation are capable of emitting approximately ten times higher power levels of radiation in pulse operation, and the combined effect of the plurality of transmitters can result in a considerable energy concentration within the volume at which they are focused. According to the present invention microwave pulses of up to a few kilowatts can act on locally narrowly defined body areas and reliably destroy malignant cells.

In order to facilitate focusing of the transmitters on virtually any body part, particular mounting means for the transmitters and ring, and particular focusing means may be provided. For instance, mounting means may be provided which allow linear reciprocation of the ring along a dimension generally perpendicular to a plane containing the ring, allow rotation of the ring about its center, and allow pivoting of the ring about either of two perpendicular axes disposed in the plane of the ring.

Further, the transmitters may be mounted so that they are radially movable with respect to the ring, and slightly pivotal with respect to the ring. To facilitate focusing of the beams, radially-extending electromagnetic coils may be provided surrounding the transmitters. Proper positioning and focusing of the transmitters may be effected in response to signals generated by ultrasonic generators positioned adjacent the transmitters.

In order to enhance the effect of the radiation upon the body, a plurality of magnets may be mounted to the ring to effect a polarization and enhance conductivity of the human body and irradiate it. All operations may be suitably monitored electronically, and suitably controlled, as by utilizing conventional available computer technology.

In practicing the method according to the present invention, a human body is placed so that it is partially disposed within the ring (preferably the body extends horizontally, being supported by an apertured table). The movement of the ring and/or transmitters is effected so as to focus radiation in the areas of the body where malignant body cells or tumors are located, and energy is supplied to the transmitters. The energy may be pulsed, and may be supplied to the transmitters in sequence. The transmitters preferably are constructed and the transmitter movement and energy supplication steps are practiced, so that the diameter of each radiation beam from each transmitter is about 1–30 cm (preferably 2–10 cm.) at the center of the ring.

It is the primary object of the present invention to provide a method and apparatus for the efficient selective, locally defined heating of an object, particularly a human body having malignant cells. This and other objects of the invention will become clear from an inspection of the detailed description of the invention, and from the appended claims.

BRIEF DESCRIPTION OF THE DRAWINGS

FIG. 7 is an end view of an outer ring of the apparatus of FIG. 4, for mounting the transmitter-mounting ring of FIG. 5;

FIG. 8 is a top plan view, partly in cross-section and partly in elevation, of the ring of FIG. 7, with portions removed for clarity.

DETAILED DESCRIPTION OF THE DRAWINGS

Figure 1:
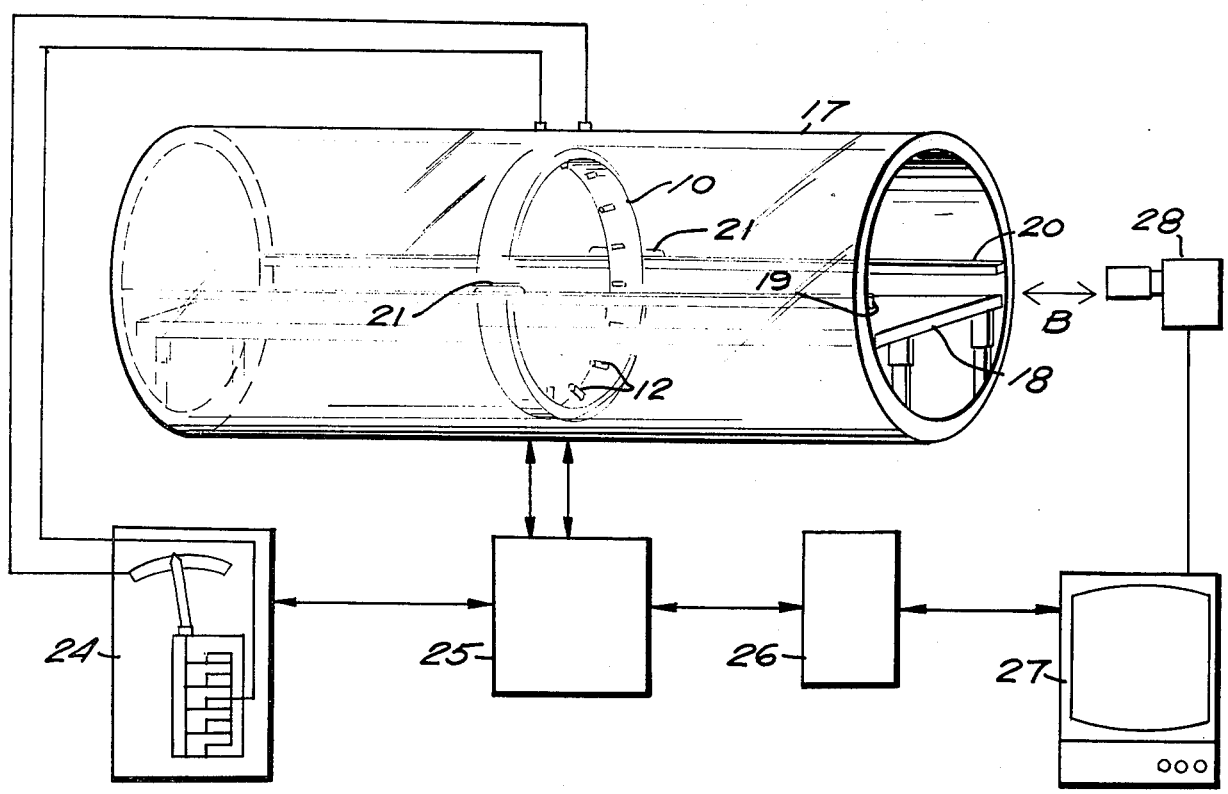
FIG. 1 is a schematic view of an exemplary heating apparatus according to the present invention.
Figure 3:
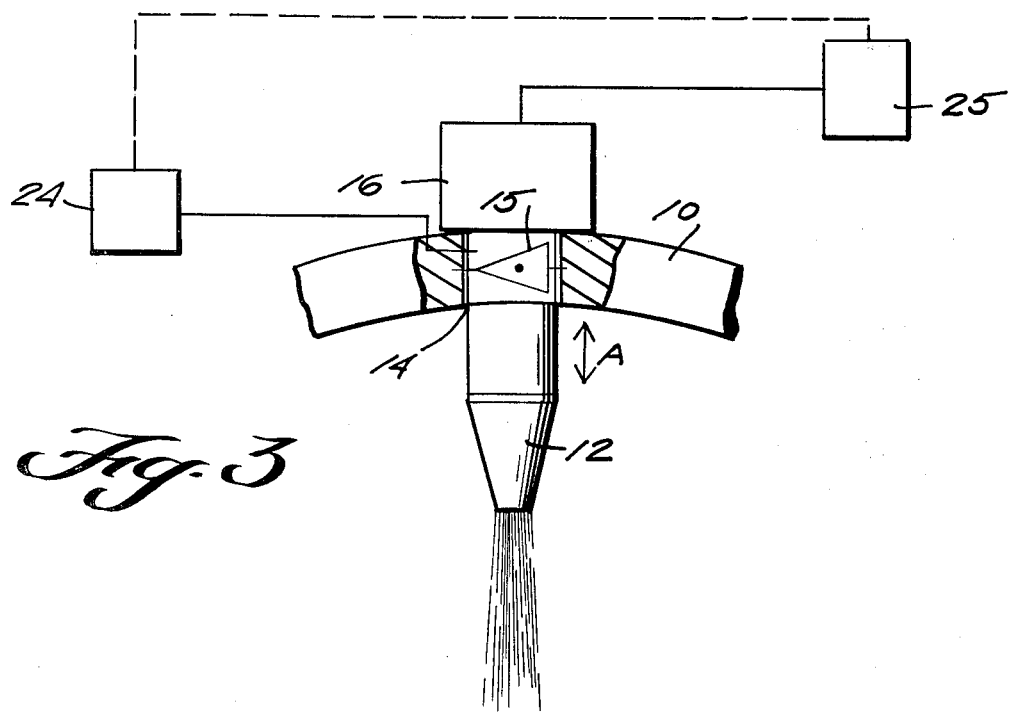
FIG. 3 is a detail schematic view, partly in cross-section and partly in elevation, illustrating a particular transmitter utilized with the ring of FIG. 2.
Figure 4:
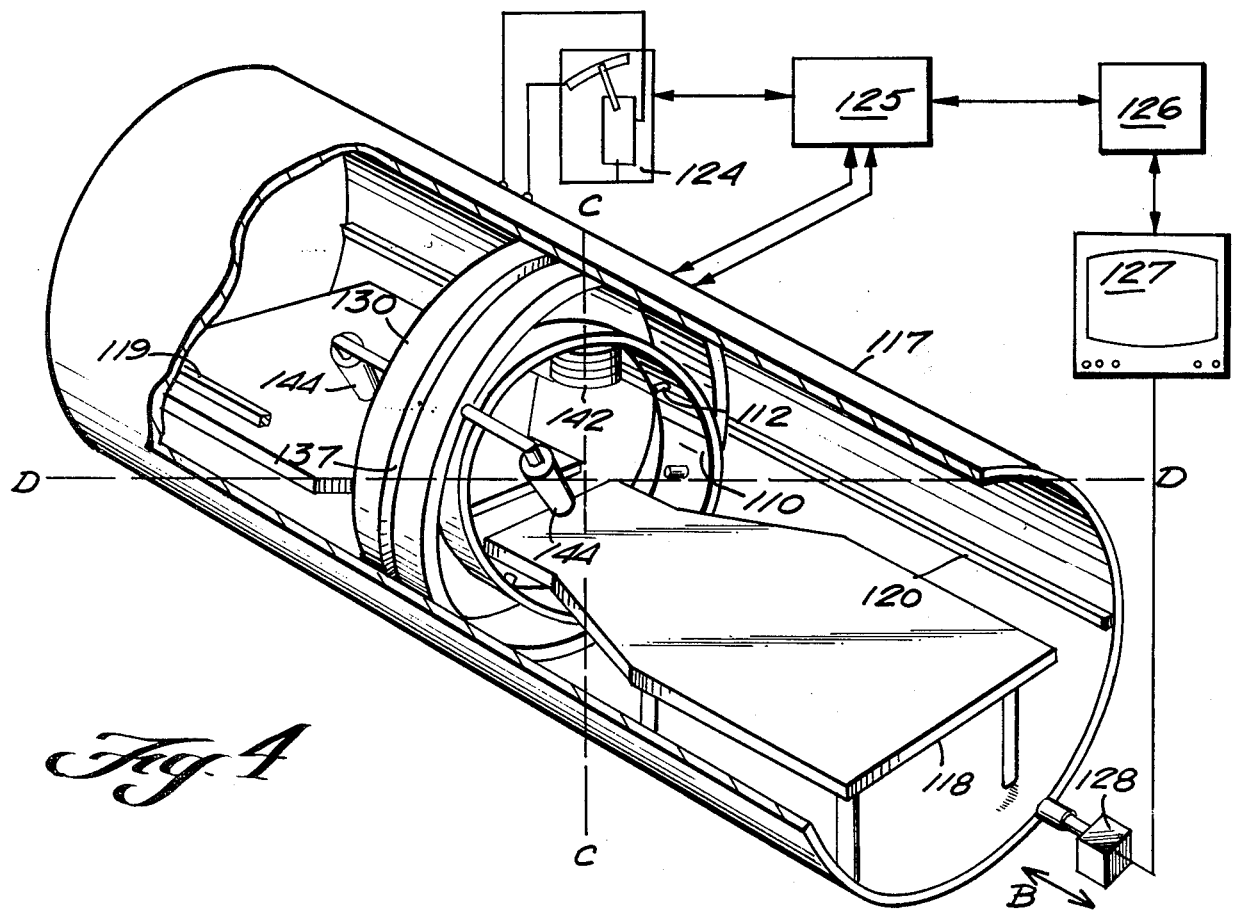
FIG. 4 is a schematic view of a second exemplary embodiment of the apparatus according to the present invention.

Exemplary apparatus according to the present invention is shown schematically in FIGS. 1 and 4. In the embodiment of FIGS. 4 through 9, like components are identified by reference numerals of components of the FIGS. 1 through 3 embodiment, except that they are preceded by a "1". In both embodiments, the apparatus is capable of the selective, locally defined heating of an object, particularly a human body to facilitate destruction of malignant cells and tumors located in the body.

Figure 2:
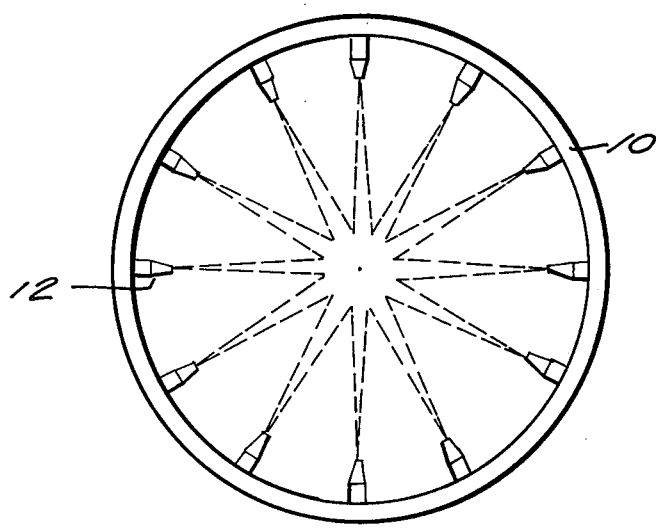
FIG. 2 is an end view of the transmitter-mounting ring of the apparatus of FIG. 1.

The apparatus of FIGS. 1 through 3 generally comprises a ring 10 and a plurality of high frequency heat radiation-emitting transmitters 12. The transmitters 12 may comprise laser sources, however preferably they comprise microwave antennas, such as solid-state microwave antennas having a low continuous power output but a high pulse power output. Energy is supplied to the transmitters 12 in any desired sequence or pulsation, transmitters 12 in turn emitting microwave beams which are directed generally interiorly of the ring 10. Means are provided for mounting the transmitters 12 to the ring 10 so that the radiation beams emitted thereby intersect each other generally within a common volume generally encompassed by the ring 10 (although the point of focus may, under some circumstances, be slightly outside the ring). The ring 10 may be segmented, continuous, perforated, or any other suitable configuration for appropriately mounting the transmitters 12 to effect the desired purpose.

Means for mounting the transmitters 12 to the ring 10 so that radiation beams emitted thereby intersect each other generally within a common volume generally encompassed by the ring are illustrated schematically in FIG. 3. Transmitter 12 may be mounted in a bore 14 in ring 10 allowing radial movement (see arrows A) of the transmitter 12 with respect to the ring 10. This allows the transmitters 12 to be focused on points located eccentrically in the ring. Also, means may be provided, shown schematically in FIG. 3 as a cone-shaped shell 15, to allow limited pivotal movement of the transmitters 12 to allow a more precise setting of eccentrically positioned irradiation points. Thus, while the transmitters 12 are normally focused on volumes or points within the ring plane, they may be focused on points located outside the plane of the ring. Positioning of the transmitters 12 with respect to the ring 10 may be accomplished manually, or utilizing a power device, such as a solenoid shown schematically at 16 in FIG. 3. The frequency range of the transmitters 12 is generally on the order of 100 mHz to 1000 mHz.

The apparatus according to the present invention also comprises means for mounting the ring 10 so that it is disposed in a generally vertical plane (although it can be movable therefrom, as hereinafter described), and such mounting means may comprise a horizontally extending shield tube 17. The diameter of the tube 17 is such that a human body can be housed therein disposed on a table 18. The tube 17 need not necessarily be solid-walled, but may comprise foil carried by a frame which reflects high frequency radiation. In FIG. 1, the tube 17 is illustrated as transparent only for clarity of illustration.

Means are also provided for mounting the ring 10 so that it is linearly reciprocal in the dimension B (see FIG. 1), which is generally perpendicular to the plane of the ring 10 and generally parallel to the position of a human body extending through the ring 10. Such mounting may be provided by a pair of horizontally extending rails 19, 20, disposed within the interior of the tube 17 on opposite sides thereof, and flanges, rollers, or the like 21 disposed on the ring 10 for engaging the rails 19, 20 to provide for movement of the ring 10 therealong.

Control components for positioning and actuating the ring and transmitters 12 are illustrated schematically in FIG. 1. Power is supplied to the transmitters 12 by the control device 24, while the spatial setting of the transmitters 12 in the ring is controlled by the setting device 25. The level of energy to be supplied to the transmitters 12 is controlled by the control device 24, either manually or automatically (e.g., by computer 26), and the energy may be supplied either simultaneously or sequentially. When the transmitters 12 are energized sequentially, the effect is that of a rotating ring.

A monitor 27 may be interconnected to computer 26 and a television camera 28 or the like. The camera 28 monitors the radiation within shield tube 17, and indicates the energy level set by the control device 24.

In the embodiment illustrated in FIGS. 4 through 9, the same basic functions are performed as in the FIGS. 1 through 3 embodiment, however there is greater control over the positioning of the transmitters 12 with respect to the object or human body being irradiated, allowing more precise and effective destruction of malignant cells or the like. In this embodiment, the center of table 118 has an opening formed therein to permit unimpeded irradiation from below the table, the opening being wide enough to accommodate the normal range of adjustability of the transmitter 112 positions with respect to a human body disposed on table 118.

Figure 9:
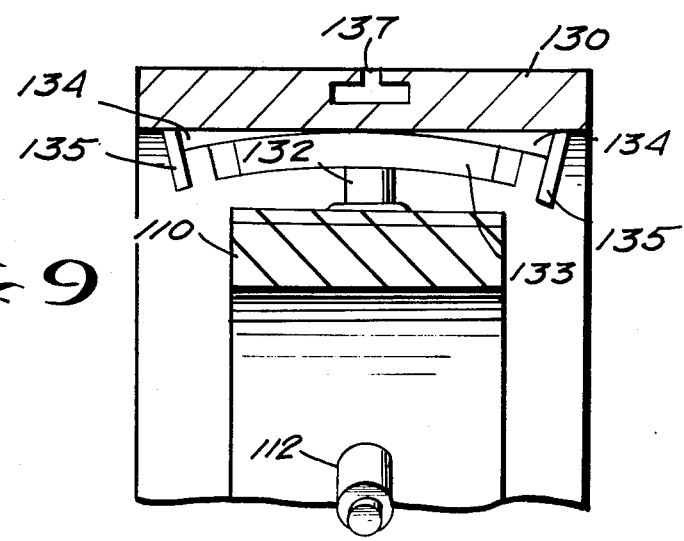
FIG. 9 is a top detail view, partly in cross-section and partly in elevation, illustrating an exemplary manner of innerconnection of the rings of FIGS. 5 and 7.

In this embodiment, means are provided for mounting the ring 110 so that it is pivotal about two perpendicular axes, e.g., axes C—C and D—D (see FIG. 4). These two perpendicular axes, C—C and D—D, preferably are generally disposed in the plane of the ring 110. Any suitable mechanism, such as gimbal rings, hemispherical sections, or the like can be provided for effecting this mounting of the ring 110. In the exemplary embodiment illustrated in the drawings, an outer ring 130 is provided about which the ring 110 is pivotal. The pivoting action is accomplished (see FIGS. 5, 7 and 9 in particular) by journal pins 132 extending radially outwardly from opposite ends of ring 110, and received by bearings 133 mounted interiorly of outer ring 130. As illustrated in FIGS. 7 and 9, the bearings 133 may be shaped as portions of cylinders, and may be received by complementary cylindrical portions 134 rigidly attached to the interior of ring 130 and receiving the bearings 133. Thus relative movement between the bearings 133 and the cylindrical sections 134 is possible. Stops 135 may be provided on the segments 134 to limit the pivotal movement of the ring 110 about axis C—C. Again, it is noted that the embodiment illustrated in the drawings is merely exemplary and other type of gimbal ring and hemispherical section structures may be provided to achieve the desired results.

Additionally, according to the present invention the outer ring 130 may be constructed so that it is rotatable about its center, the ring 110 thus necessarily being rotatable with the outer ring 130. Rotation of the outer ring 130 may be accomplished utilizing means defining an annular slot 137 (see FIGS. 4, 8 and 9 in particular) therein. A guiding structure 138 (FIG. 8), associated with each reciprocating member 121 engaging the rails 119, is disposed within the keyway defined by slot 137 to allow relative rotation of ring 130 with respect to the rails 119, 120.

In the case of all of the mounting structures allowing relative movements between components, relative movement may be accomplished manually or automatically, and suitable conventional latching structures may be provided for latching the various components in relative positions to which they have been moved.

To facilitate proper positioning of the components of the device relative to each other, a plurality of ultrasonic generators 140 may be provided, for instance one generator 140 associated with each transmitter 112. As illustrated most clearly in FIGS. 4 through 6, the generators 140 are mounted on the inside of ring 110, adjacent a transmitter 112. The generators 140 are also controlled by the control device 124, and when actuated provide indications as to whether high frequency radiation obstacles, such as bones, are located in the path of the transmitters 112. Data (signals) from energization of the ultrasonic generators (which may be simultaneous or sequential) is then utilized, either automatically or via operator control, for repositioning the ring 110 to minimize the obstruction of the transmitter 112 beam paths by bones, or the like, in the body.

Figure 5:
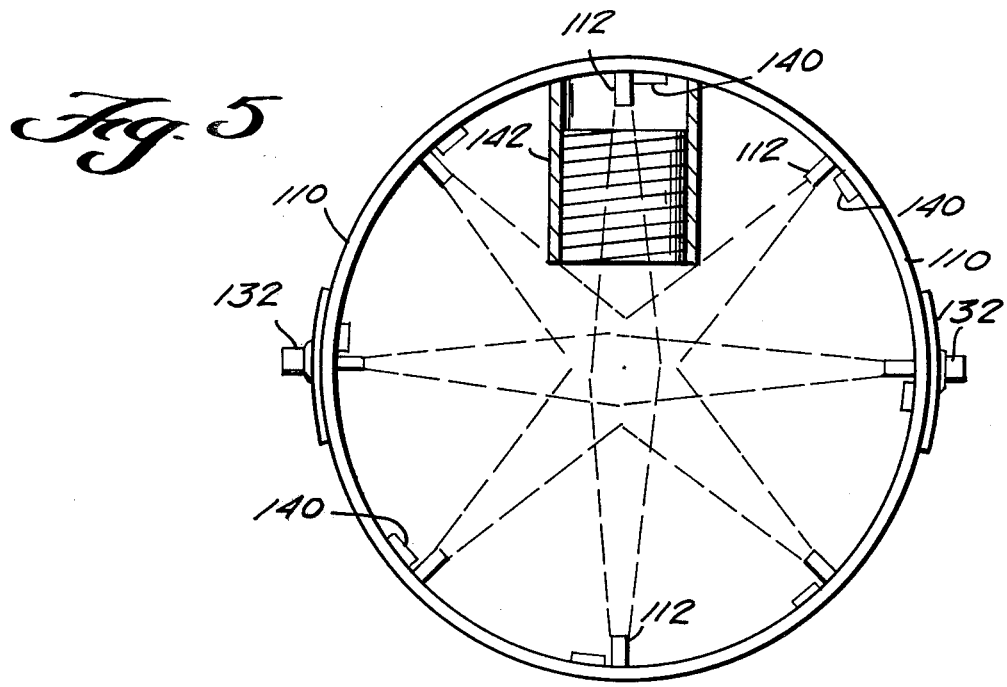
FIG. 5 is an end view of the transmitter-mounting ring of the apparatus of FIG. 4.
Figure 6:
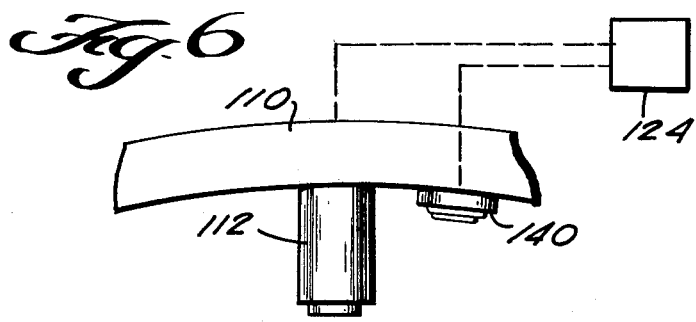
FIG. 6 is a detail schematic view of a transmitter and associated ultrasonic generator associated with the ring of FIG. 5.

Focusing of the beams from the transmitters 112 may be facilitated utilizing electromagnetic coils, such as focusing coil 142 illustrated in FIG. 5. The electromagnetic coil or solenoid 142 is also controlled by the control device 124, and a coil 142 may be associated with each transmitter 112 if desired. Energization of the coil 142 at the time its associated transmitter 112 is energized enhances the penetrability of the high frequency radiation emitted by transmitter 112. An alternative location of the transmitting coils 142 may be suspended from the outer ring 130, or shield tube 117 in such a way that upon rotation of the inner ring one of the transmitters 112 can direct its beam through a coil 142 onto the body being irradiated.

As illustrated in FIGS. 4, 7 and 8, according to the present invention a plurality of magnets 144 may be provided mounted on outer ring 130 and directed toward the central volume of the rings 130, 110, where a human body to be treated would be positioned. Any number of such magnets 144 may be utilized, and they function to bring about a polarization and consequently a better conductivity of the tissue being treated. The magnets 144 may be mounted on telescopic arms provided with articulations in order to ensure proper positioning thereof despite the orientation of the ring 110 with respect to the outer ring 130.

Utilizing the apparatus heretofore described, a method of treating a human body to destroy malignant body cells or tumors may be practiced. The method comprises the following basic steps: (a) Placing the human body (on table 7) so that it is partially disposed within the ring 10, 110. (b) Effecting movement of the ring 10, 110 and/or transmitters 12, 112 so as to focus the high frequency radiation emitted thereby in the area of the human body where malignant body cells or tumors are located. And (c) supplying energy to the transmitters 12, 112, utilizing control devices 24, 25, and 26 or 124, 125 and 126, to effect application of radiation to the area of the body where malignant body cells or tumors are located. Preferably the transmitters are constructed and steps (b) and (c) are practiced so that the diameter of each radiation beam from each transmitter is about 1-30 cm. (preferably 2-10 cm.) generally at the center of the ring 10, 110. The controls 24 through 26, 124 through 126, may supply energy and pulses to the transmitters 12, 112 or may energize the transmitters 12, 112 in sequence.

Where the plurality of ultrasonic generators 140 are utilized, the method comprises the further steps of directing ultrasonic beams from the generators 140 onto the body to determine the body part (e.g., bone) locations and the like, and step (b) is practiced in response to the signals received from the ultrasonic generators 140. Further, step (b) is practiced by practicing at least one of the following steps: linearly reciprocate the ring 10, 110 along a dimension (B) parallel to the body being treated; rotate the ring 110 (utilizing innerconnections 137, 138 between outer ring 130 and shield tube 117) about its center; pivoting the ring 110 about either of two perpendicular axes C—C and D—D, perpendicular to the body being treated in general in the plane of the ring 110 (as by pivoting ring 110 about journals 132, and pivoting journal bearings 133 with respect to cylindrical sections 134); pivoting the transmitters 12 about their connection to the ring 10; and radially moving the transmitters 12 with respect to the ring 10 (as by utilizing solenoid 16).

In practicing the method according to the invention, a metal reflector plate may be positioned above and below the table 18, 118 and the body to be irradiated can be placed between the plates. The plates form a capacitor, with one of the plates being provided with a hole for the passage of high frequency radiation. The plates can also be rotated about the body to be irradiated and may be either flat or curved. The plates facilitate polarization of the body to be irradiated, and thus assist the high frequency radiation due to the increased conductivity resulting from the polarization. In this way, such plates would act in basically the same manner as the magnets 144.

While the invention has been described primarily with respect to the treatment of malignant cells and tumors in human bodies, it will be apparent that the apparatus according to the invention is capable of performing a wide variety of other functions. For example, the apparatus may be utilized to effect cauterization (stereotactic action) without requiring cutting open the body. Further, additional high frequency transmitters may be positioned along the inner walls of the tubes 17, 117 to be utilized for whole-body irradiation if an overall temperature increase of the body is desired. This effects body temperature rises, compatible with "fever therapy" techniques, raising the body temperature to 102.2° to 113° F. (preferably 107.6° F.). Additionally, other structures besides human bodies may be heated according to the invention to perform a wide variety of intended functions.

It will thus be seen that according to the present invention, a simple yet effective method and apparatus have been provided for the selective, locally defined heating of an object, particularly the human body for the purpose of destroying malignant body cells or tumors.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent apparatus and methods.

What is claimed is:

1. Apparatus for the selective, locally defined heating of an object, comprising:
   a ring;
   a plurality of high-frequency radiation-emitting transmitters for heating an object upon which the radiation therefrom is directed;
   means for mounting said transmitters to said ring so that radiation beams emitted by said transmitters intersect each other generally within a common volume generally encompassed by said ring;
   a radially-extending electromagnetic coil surrounding at least one of said transmitters and comprising means for facilitating focusing of the radiation emitted by said at least one said transmitter;
   means for mounting said ring so that it is pivotal about two perpendicular axes and is reciprocal along a dimension perpendicular to a plane containing said ring;
   a plurality of ultrasonic generators;
   means for mounting said ultrasonic generators on an inner-surface of said ring, each adjacent a transmitter; and
   control means, responsive to signals from said ultrasonic generators, for positioning said ring.

2. Apparatus as recited in claim 1 wherein said transmitters are laser sources.

3. Apparatus as recited in claim 1 wherein said means for mounting said ring comprising an outer ring operatively connected to said ring.

4. Apparatus as recited in claim 1 further comprising a horizontally extending tube; and means for mounting said ring to said tube so that said ring is linearly reciprocal along the length of said tube.

5. Apparatus for selective, locally defined heating of an object, comprising:
   a ring;
   a plurality of high-frequency radiation-emitting transmitters for heating an object upon which the radiation therefrom is directed;
   means for mounting said transmitters to said ring so that radiation beams emitted by said transmitters intersect each other generally within a common volume generally encompassed by said ring;
   means for mounting said ring so that it is pivotal about two perpendicular horizontal axes, said mounting means comprising an outer ring operatively connected to said ring;
   means for mounting said ring for rotation about the center thereof, said rotation mounting means including an outer circumferential groove formed in said outer ring, and non-rotatable means receiving said groove at spaced points therealong; and
   means for mounting said non-rotatable means for reciprocal linear movement in a dimension perpendicular to a plane containing said ring, said means for mounting said non-rotatable means comprising a shield tube and a pair of opposite, spaced, horizontally-extending rails mounted within said shield tube.

6. Apparatus as recited in claim 5 further comprising a plurality of magnets, and means for mounting said magnets on said ring so that they effect a polarization and enhanced conductivity of the object to be irradiated by said transmitters, to enhance the effect of the irradiation.

7. Apparatus as recited in claim 5 wherein said means for mounting said transmitters to said ring comprises means for mounting said transmitters for slight pivotal movement with respect to said ring.

8. Apparatus as recited in claim 5 further comprising a radially-extending electromagnetic coil surrounding at least one of said transmitters.

9. Apparatus as recited in claims 1 or 5 further comprising means for energizing said transmitters sequentially.

10. Apparatus as recited in claim 5 further comprising a plurality of ultrasonic generators; and means for mounting said ultrasonic generators on an inner surface of said ring, each adjacent a transmitter.

11. Apparatus as recited in claim 10 further comprising control means, responsive to signals from said ultrasonic generators, for positioning said ring.

12. Apparatus as recited in claims 1 or 5 further comprising means for regulating the amount and frequency of the energy supplied to the transmitters.

13. Apparatus as recited in claims 1 or 5 wherein said means for mounting said transmitters to said ring comprises means for mounting said transmitters for radial movement with respect to said ring.

14. Apparatus as recited in claim 1 or 5 wherein said transmitters are microwave antennas.

15. Apparatus as recited in claim 14 wherein said microwave antennas are solid state antennas having a low continuous power output but a high pulse power output.

* * * * *